(12) United States Patent
Shipp

(10) Patent No.: US 8,834,362 B2
(45) Date of Patent: Sep. 16, 2014

(54) SPECULUM BLADE EXTENDER

(76) Inventor: Dane Maxwell Shipp, Solana Beach, CA (US)

( * ) Notice: Subject to any disclaimer, the term of this patent is extended or adjusted under 35 U.S.C. 154(b) by 0 days.

(21) Appl. No.: 13/021,918

(22) Filed: Feb. 7, 2011

(65) Prior Publication Data

US 2011/0196209 A1 Aug. 11, 2011

Related U.S. Application Data

(60) Provisional application No. 61/302,156, filed on Feb. 7, 2010.

(51) Int. Cl.
*A61B 1/32* (2006.01)
*A61B 1/303* (2006.01)

(52) U.S. Cl.
CPC .. *A61B 1/32* (2013.01); *A61B 1/303* (2013.01)
USPC ............................. 600/215; 600/186; 600/195

(58) Field of Classification Search
USPC .................. 600/201–203, 214–215, 219, 220
See application file for complete search history.

(56) References Cited

U.S. PATENT DOCUMENTS

| | | | |
|---|---|---|---|
| 3,841,317 A * | 10/1974 | Awais | 600/203 |
| 3,851,642 A * | 12/1974 | McDonald | 600/212 |
| 4,492,220 A | 1/1985 | Hayes | |
| 4,615,334 A * | 10/1986 | Jaeger | 600/195 |
| 4,807,600 A | 2/1989 | Hayes | |
| 5,007,409 A * | 4/1991 | Pope | 600/203 |
| 5,072,720 A | 12/1991 | Francis | |
| 5,243,966 A | 9/1993 | Ng | |
| 5,460,165 A | 10/1995 | Mayes | |
| 6,036,638 A | 3/2000 | Nwawka | |
| 6,432,048 B1 | 8/2002 | Francois | |
| 6,902,530 B1 | 6/2005 | Pianka | |
| 7,063,664 B2 | 6/2006 | Mohajer | |
| 7,081,090 B2 | 7/2006 | Strong | |
| 7,311,663 B2 | 12/2007 | Marcotte | |
| 7,654,953 B2 | 2/2010 | Borodulin | |
| 7,896,806 B2 | 3/2011 | Shah | |
| 2005/0192482 A1* | 9/2005 | Carpenter et al. | 600/203 |
| 2008/0242938 A1 | 10/2008 | Larkin | |
| 2008/0269565 A1 | 10/2008 | McMahon | |
| 2008/0287744 A1 | 11/2008 | Borodulin | |
| 2008/0312508 A1 | 12/2008 | Shulman | |

\* cited by examiner

*Primary Examiner* — Nicholas Woodall
(74) *Attorney, Agent, or Firm* — Tiffany M. Baughman

(57) ABSTRACT

A speculum blade extender apparatus including a body composed of semi-rigid reusable material with first and second walls separated from and coupled together to form a cavity and extending laterally to form opposing lateral lips and extending distally to form a distal lip, such that the contact surface area of the speculum blade is increased, resulting in more efficient and accurate examinations and addressing patient and medical practitioner concerns, collectively.

9 Claims, 4 Drawing Sheets

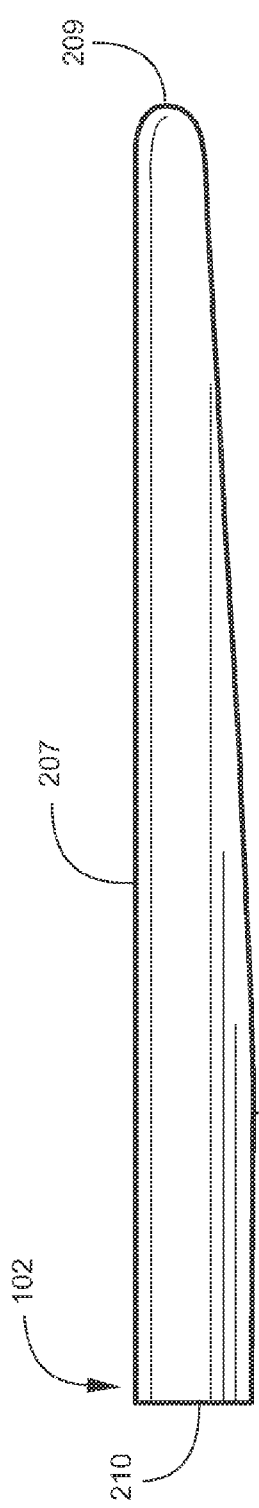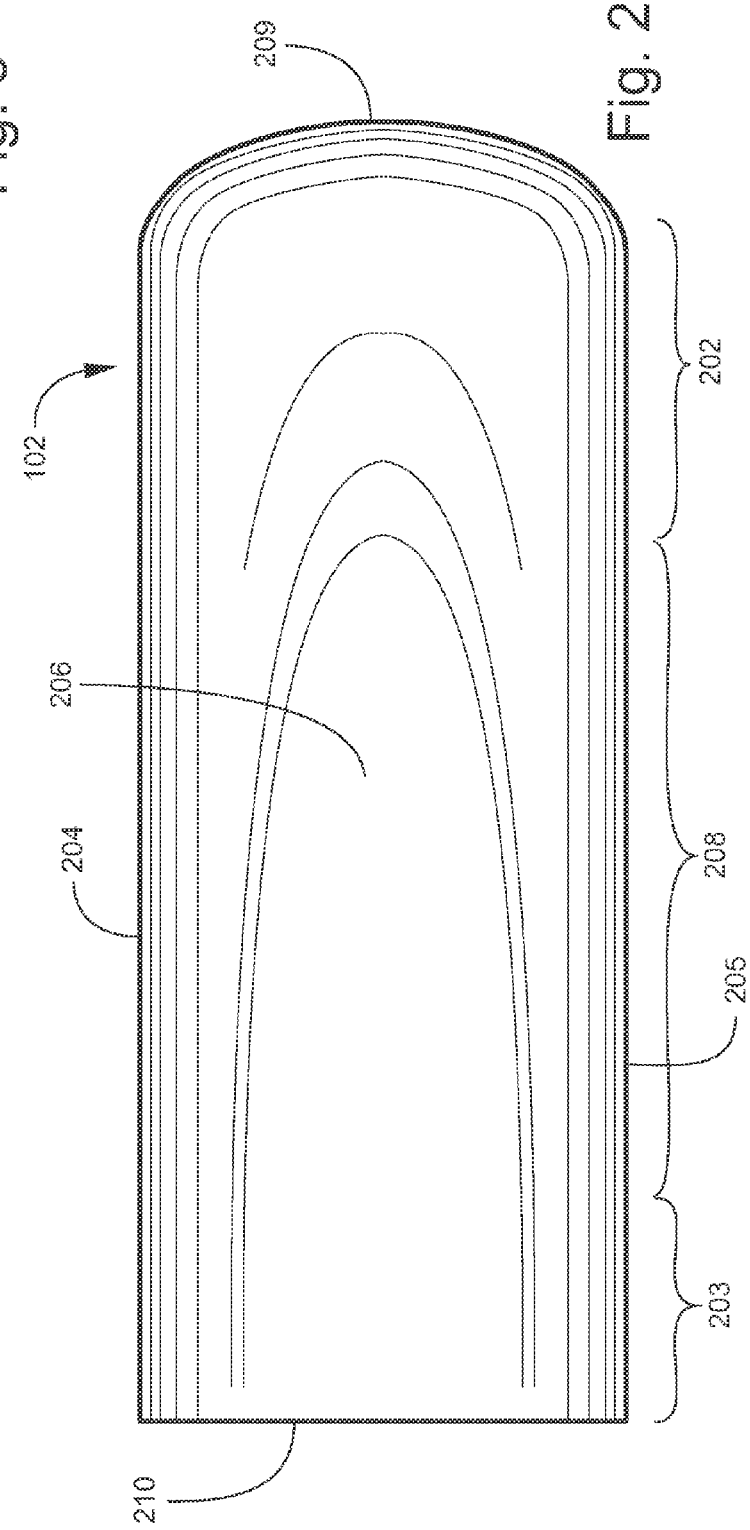

SPECULUM BLADE EXTENDER

CROSS REFERENCE TO RELATED APPLICATIONS

This application claims the benefit of U.S. Provisional Patent application Ser. No. 61/302,156 entitled "SPECULUM BLADE EXTENDER" which was filed Feb. 7, 2010. The entirety of the aforementioned application is herein incorporated by reference.

BACKGROUND

Various implementations of medical specula for use by a medical professional in enlarging an anatomical aperture in a patient's body for purposes of medical examination are widely known. Examples include, but are not limited to, nasal specula, ear specula, anal specula, and vaginal specula.

Specula are important medical instruments that serve as accurate and expedient means for providing examination and treatment of the anatomical apertures that are the subject of such examination and treatment. Specifically, a vaginal speculum is integral to the examination and treatment of the vagina and related areas. Medical practitioners require a vaginal speculum that lends itself to manual dexterity. The design of the conventional vaginal speculum enables the blades to be sufficiently movable to provide not only parallel but angularly displaced adjustment of the blades over a wide range of separation.

A known speculum is disclosed in U.S. Pat. No. 4,807,600 to Hayes. Speculum includes a handle and an adjustable arm coupled to the handle about a hinge. A first blade is integrally formed with handle, and a second blade is integrally formed with the adjustment arm. A first blade is a lower blade of the speculum, and second blade is an upper blade. Each blade includes an inner surface and an outer surface, where the outer surfaces are those surfaces oriented to contact tissue of the patient. Movement of a thumb piece results in moving upper blade relative to lower blade about a hinge. A locking device is provided to secure thumb piece in position to maintain a desired position of blades during a gynecological exam.

There are other known speculum configurations, but generally each configuration includes a rigid lower blade and a rigid upper blade, both blades composed of metal such as stainless steel or rigid plastic material. During use, the blades are closed together and inserted in combination into the vaginal cavity. Thumb piece is depressed to separate upper blade from lower blade, thus expanding the walls of the vaginal cavity. Locking device is engaged to secure blades in their desired position. The medical practitioner is then able to examine and treat the vagina, vaginal sidewalls, and uterine cervix.

Speculum configurations composed of stainless steel are preferred by many medical practitioners due to both cost and waste concerns involved in use of disposable plastic alternatives. However, due to mass production of solid components that can result in sharp, uneven edges, use of conventional speculum composed of stainless steel can result in patient discomfort. Both plastic composed and stainless steel composed speculum in most conventional configurations include a lower blade and an upper blade with opposing concavo-convex blade surfaces that provide a concave walled viewing and access channel therebetween when separated or opened, commonly referred to as a duckbill speculum. In use, duckbill speculum can impair visibility for the medical practitioner conducting the examination and treatment, which can result in longer examination times, reduced thoroughness, decreased accuracy and increased patient discomfort.

Various types of specula blade sheaths and specula blade covers are well known. Examples of some designs for specula blade sheaths are disclosed in U.S. Pat. No. 5,460,165 and U.S. Pat. No. 5,007,409. Examples of some designs for specula blade covers are disclosed in U.S. Pat. No. 4,492,220, U.S. Pat. No. 3,851,642, and U.S. Pat. No. 4,807,600. However, speculum blade covers and sheaths known in the prior art fail to provide lateral and distal extension capabilities. The prior art discloses devices that are both disposable and reusable. In addition, the prior art discloses devices that address medical practitioner concerns or patient concerns, individually. The present invention differs from these examples. The present invention is composed of soft, flexible, reusable silicone and provides extension capabilities not disclosed in the prior art. Further, the prior art does not adequately address both medical practitioner and patient concerns, collectively.

The present invention improves on the prior art by providing a device that resolves both medical practitioner and patient concerns. The present invention increases visibility of the vagina, vaginal sidewalls, and uterine cervix whereas the prior art does not disclose blade covers or sheaths that provide extension or expansion capabilities. Medical practitioners that perform pelvic examinations infrequently can use the present invention with its extension capabilities to perform more accurate, efficient, and comfortable examinations. The present invention is composed of semi-rigid silicone material which causes less tissue trauma. By example, women ranging from atrophic postmenopausal women to nulliparous women to virginal women can be easily emotionally and physically traumatized by metal and plastic speculums resulting in bleeding and pain that can affect the accuracy, thoroughness and duration of examinations. The present invention provides for interchangeable blade extenders of different sizes to customize a speculum to a patient's anatomical design. Further, the present invention is comprised of extenders that are standardized to fit a small size speculum and will, therefore, reduce medical practitioners' requirements to purchase multiple sized specula. The present invention is reusable and sterilizable resulting in reduced waste.

Further, the present invention also addresses patient concerns such as comfort. Some women may be averse to scheduling routine or medically necessary pelvic examinations due to fear of discomfort or pain. Further, a patient may have access to only one, novice medical practitioner in a rural or disadvantaged area and may avoid an examination. The present invention provides a more comfortable, more efficient, user-friendly design that can relieve these fears and uncertainties.

Therefore, it is an object of the present invention to provide a device that addresses the concerns of both medical practitioner and patient.

SUMMARY

One implementation provides a reusable speculum blade extender. A body of semi-rigid, reusable material having a proximal end portion spaced from a closed distal end portion along a longitudinal axis, the body including a first wall separated from and coupled to a second wall to form a cavity, the cavity having an opening located at the proximal end portion of the body, the cavity having opposing lateral boundaries and a distal boundary such that a speculum blade inserted therein is limited from movement, the first wall coupled to the second wall along the lateral boundaries and the distal boundary to form a compound closed surface, the compound closed surface extending laterally beyond the lateral boundaries of the cavity to form a lateral lip, the compound closed surface further extending longitudinally beyond the distal boundary of the cavity to form a distal lip, such that contact surface area of the blade is increased.

BRIEF DESCRIPTION OF THE DRAWINGS

FIG. 2 is a perspective top view of a reusable speculum blade extender according to one implementation.

FIG. 3 is a perspective side view of speculum blade extender shown in FIG. 2.

DETAILED DESCRIPTION OF THE INVENTION

Blade extender for placement on speculum and methods for using such speculum blade extender are described herein.

Figure 1:
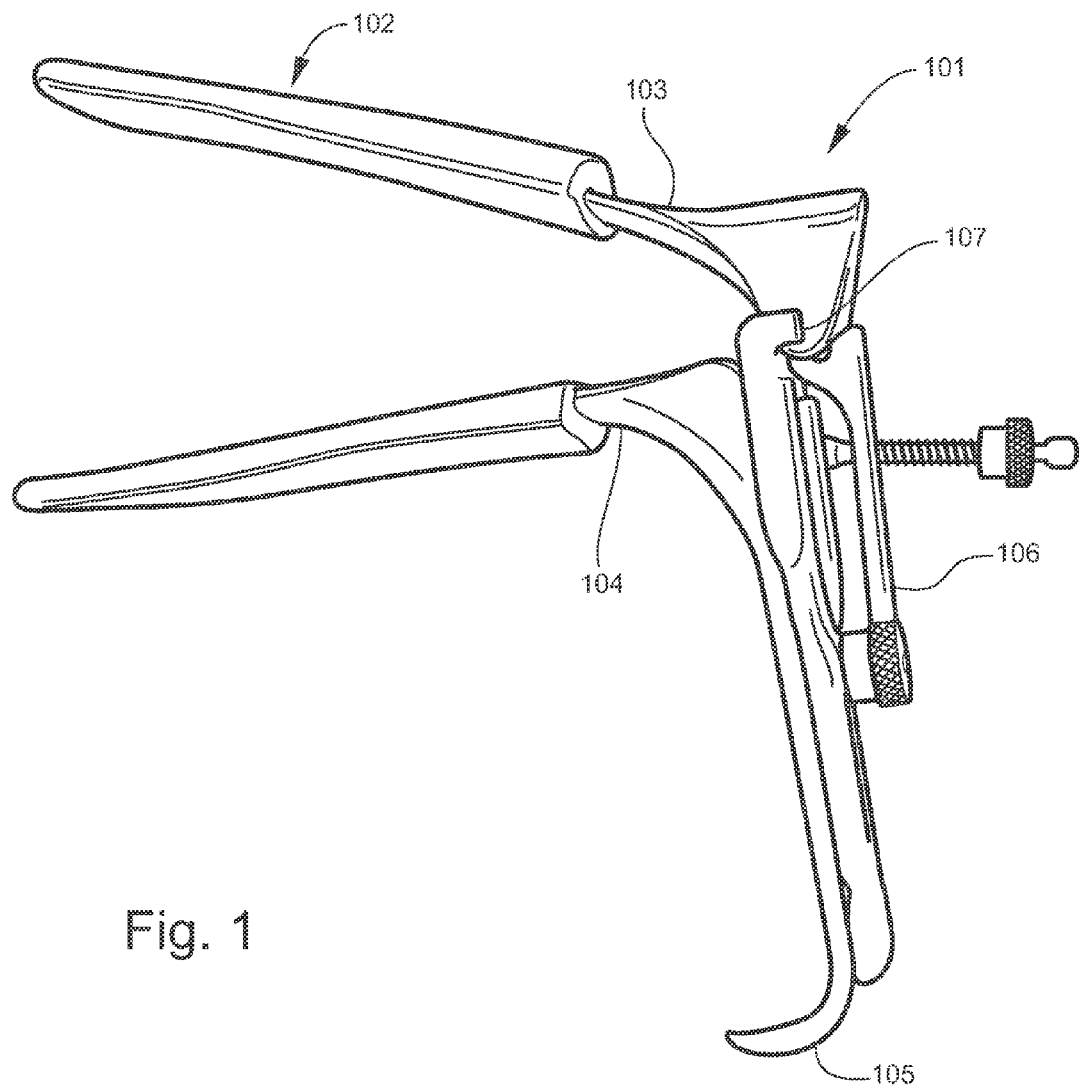
FIG. 1 is a perspective view of a vaginal speculum with extender blades attached to both upper and lower speculum blades according to one implementation.

FIG. 1 is a perspective view of a vaginal speculum with extender blades attached to upper and lower speculum blades. A preferred implementation of the present invention consists of a reusable extender blade 102 designed to be used with a vaginal speculum 101 having a pair of opposing parallel blades 103, 104. A handle 105 is formed integrally with the lower blade 104 and a thumb press 106 may be used to pivot the lower blade 104 away from the upper blade 103 about a pivot axis 107 located at the proximal ends.

Figure 5:
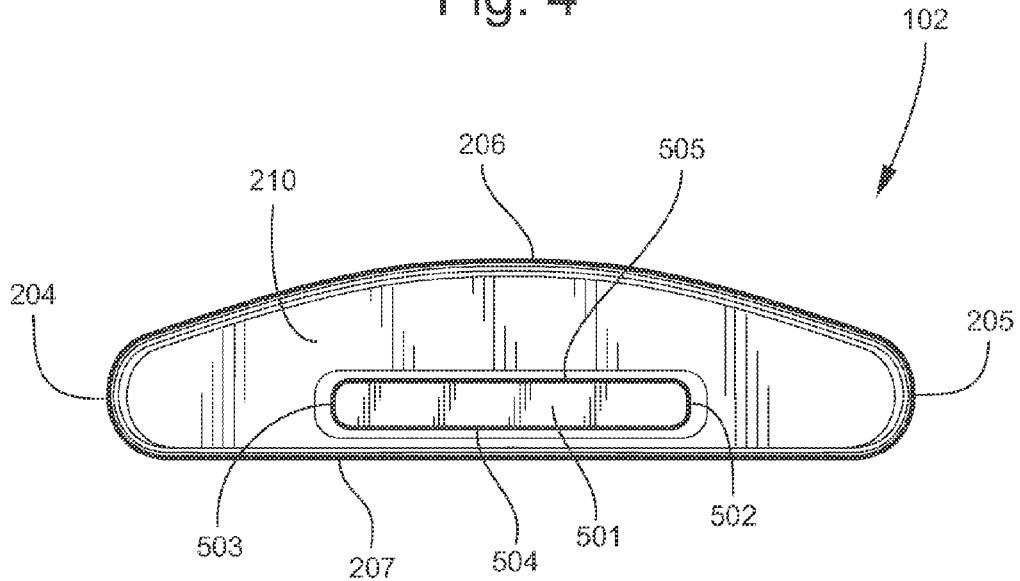
FIG. 5 is a perspective view of proximal end portion of speculum blade extender shown in FIG. 2 illustrating cavity for receiving speculum blade.

FIG. 2 is a perspective top view of a speculum blade extender 102 according to one implementation. Speculum blade extender 102 includes a proximal end portion 203 spaced from a distal end portion 202, a longitudinally extending first side or edge 205 generally opposite a longitudinally extending second side or edge 204, and a first wall 206 separated from and coupled to a second wall 207 (as illustrated in FIG. 3). Opposing sides or edges 204, 205 form opposing lateral sides or edges 204, 205 of extender 102, and walls 206, 207 are generally oriented along a longitudinal axis. As illustrated in FIG. 5, sides 204, 205 and walls 206, 207 cooperate to define a pocket or cavity 501 configured to receive one of speculum blades.

FIG. 5 is a perspective view of speculum blade extender 102 illustrating one implementation of a cavity 501. In the preferred implementation, a central portion of first wall 206 is relieved or otherwise removed to define a cavity 501 that extends longitudinally from proximal end portion 203 to distal edge of center portion 208. Cavity 501 is formed as part of first wall 206, which is separated and offset from an inner surface of second wall 207, in a manner that defines cavity 501. Cavity 501 is configured to allow insertion of speculum blade 103. Proximal end 210 of extender 102 provides an opening 501 which allows speculum blade 103 to be inserted within the extender 102.

Figure 6:
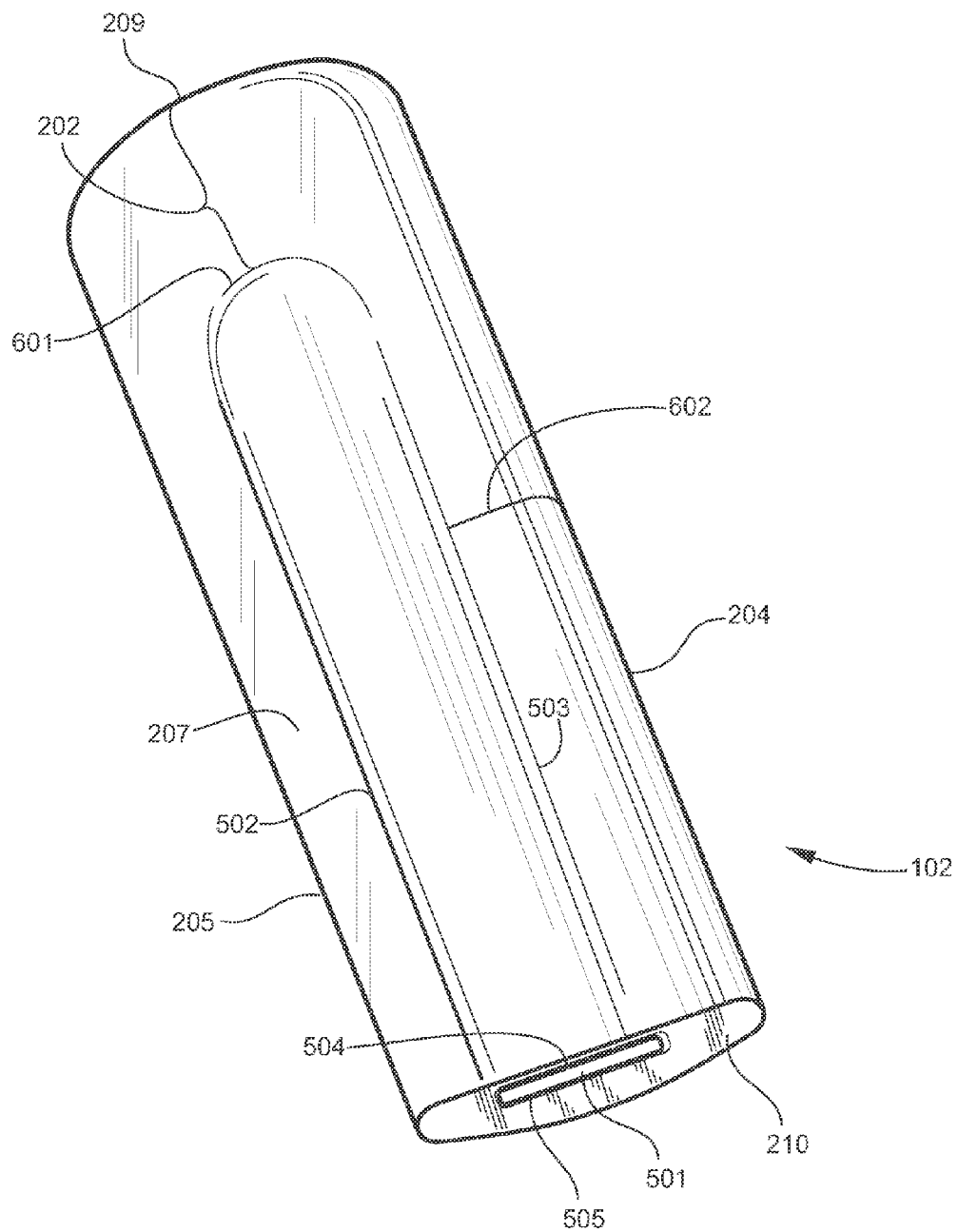
FIG. 6 is a perspective bottom view of speculum blade extender in FIG. 2 illustrating lateral and distal boundaries of cavity.

The cavity 501 having upper 505, lower 504, and lateral 502, 503 boundaries formed by the coupling of the first 206 and second 207 walls into a generally compound closed bilateral surface. As illustrated in FIG. 6, the cavity 501 having distal boundary 601 formed by the coupling of the first 206 and second 207 walls into a generally compound closed distal surface 202. The upper 505, lower 504, lateral 502, 503, and distal 601 boundaries serve to restrict the speculum blade 103 from free movement.

Figure 4:
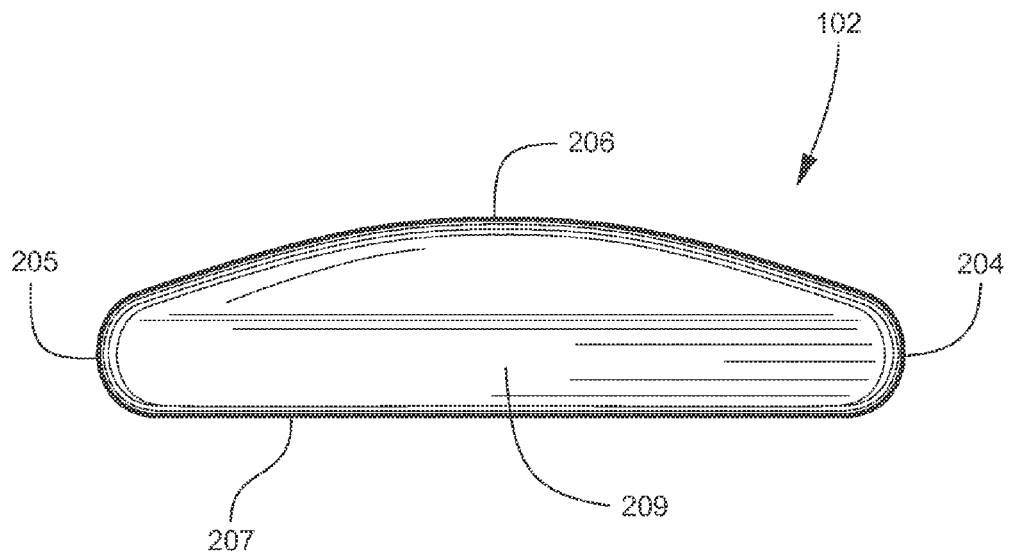
FIG. 4 is a perspective view of distal end portion of speculum blade extender shown in FIG. 2.

FIG. 4 is a perspective view of distal closed end portion 202 of speculum blade extender 102. Lateral side or edge portion 204 defines a generally compound closed surface formed by the confluence of walls 206, 207 smoothly blending to lateral edge 204. As illustrated in FIG. 6, the compound closed surface formed by the coupling of the first 206 and second 207 walls extends beyond the opposing lateral boundaries 502, 503 of the cavity 501 to the opposing lateral sides 204, 205 creating a lateral lip 602. In the preferred implementation, the lateral lip 602 on opposing sides of the cavity 501 terminates in a tapered lateral edge 204. However, it is contemplated that the lateral lip 602 terminates in a blunt lateral edge or other edge.

FIG. 6 is a perspective bottom view of a speculum blade extender 102 in accordance with one implementation. Proximal end portion 203 extends from a proximal end 210 of extender 102 to a central portion 208. In general, proximal end portion 203 provides an entrance into the pocket or cavity 501 that is formed between first 206 wall and second 207 wall. Distal end portion 202 extends from a distal end 209 to the central portion 208. Distal end portion 202 defines a generally compound closed surface formed by the confluence of walls 206, 207 smoothly blending to distal edge 209. The compound closed surface formed by the coupling of the first 206 and second 207 walls extends beyond the distal boundary 601 of the cavity 501 to the distal end 209 creating a distal lip 202. In the preferred implementation, the distal lip 202 terminates in a tapered distal edge 209. However, it is contemplated that the distal lip 202 terminates in a blunt distal edge or other edge.

In the preferred implementation, walls 206, 207 of extender 102 extend laterally from longitudinal axis for approximately 1-2 cm beyond opposing lateral boundaries 502, 503 of cavity 501 to increase contact surface area. With additional reference to FIG. 6, opposing lateral lips 602 of extender 102 extend laterally beyond lateral boundaries 502, 503 of cavity 501 for a prescribed length. In one implementation, distal lip 202 extends longitudinally from distal boundary 601 for approximately 1-2 cm before terminating in the distal edge 209 to increase contact surface area. With additional reference to FIG. 6, the distal lip 202 of extender 102 extends longitudinally beyond distal boundary 601 of cavity 501 for a prescribed length. Any possible combination of lateral lip 602 extension measurements and distal lip 202 extension measurements are contemplated.

It is further contemplated that extender 102 improve upon the shape and/or thickness of the traditional duckbill shaped speculum. In one implementation, extender blade 102 may be shaped alternatively to contribute to the beneficial characteristics of extender 102 disclosed herein. For purposes of example, extender 102 may comprise a blade with flat blade surface, or alternatively extender may comprise a blade with plano-concave surface to provide for enhanced visibility. In one implementation, lateral edges 204, 205 of extender 102 proximally located to the proximal end 210 of extender 102 extend 1 cm beyond lateral boundaries 502, 503 of speculum blade 103, and lateral edges 204, 205 of extender 102 distally located to the proximal end 210 of extender 102 extend 3 cm beyond lateral boundaries 502, 503 of cavity 501, so that distal end portion 202 of extender 102 is wider than proximal end portion 203. However, any combination of shapes of extender blade 102 is contemplated herein. In another implementation, extender blade 102 thickness may be increased or decreased to contribute to the beneficial characteristics of the present invention. For purposes of example, extender blade 102 comprises 2 cm thick semi-rigid material, or alternatively, proximal end portion 203 of extender blade 102 comprises 3 cm thick semi-rigid material that tapers to 1 cm at distal end portion 202 of extender blade 102. Any possible combination of thicknesses is contemplated.

In a preferred implementation, extender 102 is formed of a semi-rigid, heat resistant silicone. Use of any semi-rigid, heat resistant, reusable, sterilizable material to form extender 102 is contemplated herein. In one implementation, semi-rigid material comprising extender is transparent. However, any color or translucency of material is contemplated.

In one implementation, speculum blade extender 102 is placed on speculum 101 with small blades. Extender 102 is reusable and must be sterilized before each use. Distal end of speculum blade 103 is inserted into speculum blade extender cavity 501. Speculum blade 103 is further inserted into speculum blade extender 102 such that the distal portion of speculum blade 103 that enters a patient's vaginal cavity and comes into contact with patient's body is encompassed by extender 102, and the proximal portion of speculum blade 103 which does not enter vaginal cavity is not covered. In one implementation, two speculum blade extenders 102 are used. However, it is contemplated that one extender 102 may be placed on lower speculum blade 104 or upper speculum blade 103 exclusively. Further, it is contemplated that any combination of different lateral sized blade extenders and longitudinal lengthened blade extenders may be placed on the lower speculum blade 104 and upper speculum blade 103. For purposes of example, a speculum blade extender 102 with lateral lip 602 extending 2 cm beyond opposing lateral boundaries 502, 503 of cavity 501 and distal lip 202 extending 2 cm beyond distal boundary 601 of cavity 501 may be placed on upper speculum blade 103, and a speculum blade extender 102 with lateral lip 602 extending 1 cm beyond opposing lateral boundaries 502, 503 of cavity 501 and distal lip 202 extending 1 cm beyond distal boundary 601 of cavity 501 may be placed on lower speculum blade 104. This example would allow for increased contact surface area of the upper blade 103 resulting in increased access channel visibility between blades 103, 104 in some patients.

The speculum blade extender 102 is placed on speculum 101 such that the closed end 209 is located at end of speculum 101 distal to where the medical practitioner holds the speculum 101 and the cavity 501 is located at the end proximal to where the medical practitioner holds the speculum 101.

Once the speculum 101 is inserted into the vaginal cavity and opened, a speculum blade extender 102 provides accurate and increased visibility of the vaginal cavity and uterine cervix and the medical practitioner may conduct examination or treatment rapidly and efficiently. In one implementation, clear silicone will enhance visualization of vaginal mucosa.

It is further contemplated that the present invention is applicable to other medical instruments and provides similar benefits. For purposes of example, ear specula, nasal specula, anal specula, laryngoscope, surgical retractor blade extenders, and dental tools would provide for increased patient comfort, more efficient examination by the medical practitioner, and decreased exam or treatment duration. The medical devices listed above do not constitute a comprehensive or exhaustive list of devices that may benefit from the present invention.

The many features and advantages of the present invention are apparent from the detailed specification. Since numerous modifications and changes will readily occur to those of ordinary skill in the art, it is not desired to limit the invention to the exact construction and operation illustrated and described. Accordingly, all suitable modifications and equivalents may be resorted to as falling within the scope of the invention.

The invention claimed is:

1. A speculum blade extension apparatus comprising:
a body of semi-rigid, reusable material having a proximal end portion spaced from a closed distal end portion along a longitudinal axis,
the body including a first wall separated from and coupled to a second wall to form a cavity,
the cavity having an opening located at the proximal end portion of the body,
the cavity having opposing lateral boundaries and a distal boundary such that a speculum blade inserted therein is limited from movement,
the first wall coupled to the second wall along the lateral boundaries and the distal boundary to form a compound closed surface,
the compound closed surface extending laterally beyond the opposing lateral boundaries of the cavity to form opposing lateral lips that extend at least 2.0 cm beyond the lateral boundaries of the cavity in opposing directions, such that the contact surface area of speculum blade is increased,
the compound closed surface further extending longitudinally beyond the distal boundary of the cavity to form a distal lip that extends at least 2.0 cm beyond the distal boundary of the cavity, such that the contact surface area of speculum blade is increased,
the opposing lateral lips decreasing in thickness uniformly creating tapered lateral edges,
the distal lip decreasing in thickness uniformly creating a tapered distal edge.

2. The apparatus of claim 1 wherein the body is composed of semi-rigid, heat resistant, reusable, sterilizable material.

3. The apparatus of claim 2 wherein the material is translucent material.

4. The apparatus of claim 2 wherein the material is opaque material.

5. The apparatus of claim 1 wherein the distal lip and opposing lateral lips terminate in a tapered edge.

6. The apparatus of claim 1 wherein the distal lip and opposing lateral lips terminate in a blunt edge.

7. The apparatus of claim 1 wherein the opposing lateral lips extend for a shorter length at distal boundary of extender than at proximal boundaries.

8. The apparatus of claim 1 wherein the opposing lateral lips are shaped such that a plano-convex surface area is formed.

9. The apparatus of claim 1 wherein the distal lip is shaped such that a piano-convex surface area is formed.

* * * * *